United States Patent
Meine et al.

(10) Patent No.: US 11,420,918 B2
(45) Date of Patent: Aug. 23, 2022

(54) METHOD FOR PRODUCING A HYDROXY COMPOUND BY DECARBOXYLATION IN THE ABSENCE OF A CATALYST

(71) Applicant: Covestro Intellectual Property GmbH & Co. KG, Leverkusen (DE)

(72) Inventors: Niklas Meine, Düsseldorf (DE); Erik Sluyts, Brasschaat (BE); Jan Heijl, Lokeren (BE)

(73) Assignee: Covestro Intellectual Property GMBH & Co. KG, Leverkusen (DE)

( * ) Notice: Subject to any disclaimer, the term of this patent is extended or adjusted under 35 U.S.C. 154(b) by 0 days.

(21) Appl. No.: 17/295,240

(22) PCT Filed: Dec. 2, 2019

(86) PCT No.: PCT/EP2019/083213
§ 371 (c)(1),
(2) Date: May 19, 2021

(87) PCT Pub. No.: WO2020/114927
PCT Pub. Date: Jun. 11, 2020

(65) Prior Publication Data
US 2021/0395177 A1 Dec. 23, 2021

(30) Foreign Application Priority Data
Dec. 7, 2018 (EP) .................................. 18211030

(51) Int. Cl.
*C07C 37/50* (2006.01)
*C07C 37/74* (2006.01)

(52) U.S. Cl.
CPC .............. *C07C 37/50* (2013.01); *C07C 37/74* (2013.01)

(58) Field of Classification Search
CPC ................................. C07C 37/50; C07C 37/74
See application file for complete search history.

(56) References Cited

U.S. PATENT DOCUMENTS 9,206,449 B2 * 12/2015 Choi ......................... C12P 7/42
2004/0143867 A1 7/2004 Meyer et al.

FOREIGN PATENT DOCUMENTS

| DE | 2248525 A1 | 4/1973 |
| EP | 1277723 A1 | 1/2003 |
| JP | 2016023136 | 2/2016 |
| WO | 2014070742 A1 | 5/2014 |

OTHER PUBLICATIONS

International Search Report for International Patent Application No. PCT/EP2019/083213, dated Jan. 29, 2020.
Written Opinion for International Patent Application No. PCT/EP2019/083213, dated Jan. 29, 2020.

* cited by examiner

*Primary Examiner* — Sikarl A Witherspoon
(74) *Attorney, Agent, or Firm* — K&L Gates LLP

(57) ABSTRACT

The invention relates to a method for producing a specific hydroxyl compound by decarboxylating a specific carboxylic acid compound or a salt of said carboxylic acid compound in the absence of a catalyst and to a method for producing a bisphenol.

16 Claims, No Drawings

METHOD FOR PRODUCING A HYDROXY COMPOUND BY DECARBOXYLATION IN THE ABSENCE OF A CATALYST

CROSS REFERENCE TO RELATED APPLICATIONS

This application is a U.S. national stage application, filed under 35 U.S.C. § 371, of International Application No. PCT/EP2019/083213, which was filed on Dec. 2, 2019, and which claims priority to European Patent Application No. 18211030.4, which was filed on Dec. 7, 2018. The contents of each are hereby incorporated by reference into this specification.

FIELD

The present invention relates to a process for producing a specific hydroxy compound by decarboxylation of a specific carboxylic acid compound or of a salt of said carboxylic acid compound in the absence of a catalyst and to a process for producing a bisphenol.

BACKGROUND

Phenols having different substitution patterns on the aromatic ring are the starting compounds for various monomers and thus also for the polymers resulting therefrom. The production of such phenols from renewable raw materials is a major challenge. One option for producing biobased phenol is the direct fermentation of sugars, as described for example in WO 2014/076113 A1. However, phenol is toxic to the microorganism described therein and its removal from the aqueous fermentation broth is also laborious. Hydroxybenzoic acids such as 4-hydroxybenzoic acid, 2-hydroxybenzoic acid, and 3-hydroxybenzoic acid can likewise be produced from sugars by fermentation. Since they are generally less toxic to the microorganisms used, higher yields can usually be achieved compared to phenol. Hydroxybenzoic acids can be crystallized and separated from the fermentation broth. A subsequent decarboxylation of 4-hydroxybenzoic acid to phenol has also previously been described. JP 2016-23136 A describes the reaction using a heterogeneous catalyst in water as solvent. A. S. Lisitsyn in Applied Catalysis A: General 332; 2007 (166-170) describes decarboxylation in diphenyl ether using a copper catalyst. L. J. Goossen et al. in ChemCatChem 2010, 2, 430-442 describe decarboxylation using a silver or copper catalyst in NMP as solvent. Dalton Transactions (24), 4683-4688; 2009 also describes decarboxylation in toluene by electron-rich palladium complexes.

However, the methods described all use a homogeneous or heterogeneous catalyst. The use of a catalyst means that this must always be separated from the desired product at the end of the decarboxylation reaction. Although a heterogeneous catalyst can be separated more easily than a homogeneous catalyst, in both cases catalyst poisoning frequently occurs, which means that a catalyst must frequently be partly renewed, regenerated or completely replaced after a given time. This leads to additional process costs, but the resultant lowering of the activation energy of the reaction by the catalyst means these are usually accepted. Nevertheless, the described reactions have potential for improvement in respect of the reaction conditions and of their cost-efficiency in particular.

SUMMARY

The object of the present invention therefore was to provide a process for producing specific hydroxy compounds of the formula (I) by decarboxylation of a carboxylic acid compound of the formula (II) or of a corresponding salt of said carboxylic acid compound of the formula (II), thereby improving at least one disadvantage of the prior art. In particular, the object of the present invention was to provide a process that affords the hydroxy compound of the formula (I) in high cost-efficiency. The process should in particular avoid the catalyst separation step, since such an additional step is often undesirable.

At least one, preferably all, of the abovementioned objects were achieved by the present invention. It was surprisingly found that the decarboxylation of a carboxylic acid compound of the formula (II) or of a corresponding salt of said carboxylic acid compound of the formula (II) proceeds even without the use of a catalyst. In particular, this reaction also takes place on an economically viable scale. The decarboxylation reaction without the use of a catalyst allows this reaction to be carried out at points in existing processes not previously utilized for this purpose. For example, the process of the invention allows the decarboxylation to be carried out in existing distillation columns that are used for the distillative workup of hydroxy compounds of the formula (I). By adding a carboxylic acid compound of the formula (II) or a corresponding salt of said carboxylic acid compound of the formula (II) to the bottoms of these distillation columns, the hydroxy compound of the formula (I) can be taken off as a distillate largely without further energy costs and also without further expenditure on apparatus. This distillate not only comprises the hydroxy compound of the formula (I) that was originally intended to be worked up, it also comprises hydroxy compounds of the formula (I) newly formed in the column by decarboxylation. Compared to the former use of the distillation column, this gives a significantly increased yield of purified distillate, which can be used further.

The invention accordingly provides a process for producing a hydroxy compound of the formula (I)

in which
R is a linear or branched alkyl group having 1 to 6 carbon atoms,
n is 1 or 2, and
m is 0, 1, 2, or 3,
by decarboxylation of a carboxylic acid compound of the formula (II) or of a corresponding salt of said carboxylic acid compound of the formula (II)

in which R, n, and m are as defined above,
characterized in that the decarboxylation is carried out in the absence of a catalyst.

DETAILED DESCRIPTION

According to the present invention, the decarboxylation reaction is carried out without a catalyst. The definition of a "catalyst" is known to those skilled in the art. In particular, they understand a catalyst as meaning a substance that lowers the activation energy of a reaction and thus increases the reaction rate without itself being consumed in the reaction. The invention excludes the presence of such a catalyst that catalyzes the decarboxylation reaction. The term catalyst according to the invention preferably encompasses both homogeneous catalysts and heterogeneous catalysts. Particularly preferably, the process of the invention also in particular does not include a step of actively adding a catalyst. The invention particularly preferably excludes the presence in the decarboxylation reaction of a catalyst selected from the group consisting of $Al_2O_3$, $H_3PO_4$ supported on $Al_2O_3$, $PtCl_x$ supported on $Al_2O_3$, Cu/Al/Ga-MOFs, Pt-Al-MOFs, palladium supported on activated carbon, platinum supported on activated carbon, zeolites such as ZSM-5, HZSM-5, $Fe_2O_3$ supported on MCM-41 (Mobil Composition of Matter No. 41), $Fe_2O_3$ supported on Al-MCM-41, Pt supported on SAPO-34 (silicoaluminophosphate), Pt supported on SAPO-11, Pt hydrotalcite, Pt supported on $SiO_2$, a Brønsted base, and any mixtures thereof.

The process of the invention is preferably characterized in that the decarboxylation is carried out in the presence of at least one solvent. The term "solvent" is known to those skilled in the art. In particular, a solvent means that the reactants and products of the decarboxylation reaction are present in dissolved form under the reaction conditions. The terms "dissolve" and "in solution" preferably mean that, when filtering a liquid in which a substance is dissolved, no solid can be separated off using customary filter methods. It is particularly preferable that the decarboxylation reaction takes place in the liquid phase. The process of the invention preferably includes a step of actively adding at least one solvent before the start of the decarboxylation reaction. In this case, the at least one solvent can be added to the reactants or the reactants can be added to the at least one solvent.

The solvent is preferably an organic solvent having a boiling point that is higher than the boiling point of the hydroxy compound of the formula (I). For example, bisphenol A or alkylphenols are suitable for use here.

The at least one solvent is very particularly preferably selected from a hydroxy compound of the formula (I). This solvent in addition preferably corresponds to the produced compound of the formula (I).

In a preferred embodiment, the invention is characterized in that at least one hydroxy compound of the formula (I) is throughout the decarboxylation reaction present in a stoichiometric excess relative to the carboxylic acid compound of the formula (II), the decarboxylation being carried out at a temperature that is above the melting temperature both of the hydroxy compound of the formula (I) that is formed and of the at least one hydroxy compound of the formula (I) used in a stoichiometric excess.

In this embodiment, the carboxylic acid compound of the formula (II) or the salt of the carboxylic acid compound of the formula (II) is present alongside at least one hydroxy compound of the formula (I). This also applies before the start of the decarboxylation reaction. The at least one hydroxy compound of the formula (I) is present in a stoichiometric excess. This means that the carboxylic acid compound of the formula (II) or the salt of the carboxylic acid compound of the formula (II) is present in a molar deficit relative to the at least one hydroxy compound of the formula (I). During the decarboxylation, the hydroxy compound of the formula (I) is then additionally formed as a target product. This may be the same or different, preferably the same, as the at least one hydroxy compound of the formula (I). The invention thus preferably excludes the situation in which the hydroxy compound of the formula (I) forms in situ as the target product and then at some point thereafter a molar deficit of the carboxylic acid compound of the formula (II) or of the salt of the carboxylic acid compound of the formula (II) potentially develops, since at least one hydroxy compound of the formula (I) must be additionally present from the start of the decarboxylation onwards. In accordance with the invention, it is preferable that, before carrying out the decarboxylation reaction, the carboxylic acid compound of the formula (II) or the corresponding salt of the carboxylic acid compound of the formula (II) is dissolved in the at least one hydroxy compound of the formula (I) that throughout the decarboxylation reaction is present in a stoichiometric excess relative to the carboxylic acid compound of the formula (II). The carboxylic acid compound of the formula (II) or the salt of the carboxylic acid compound of the formula (II) is thus preferably soluble in the at least one hydroxy compound of the formula (I) that throughout the decarboxylation reaction is present in a stoichiometric excess relative to the carboxylic acid compound of the formula (II).

The process of the invention is in this embodiment preferably executed at a temperature that is above the melting temperature both of the hydroxy compound of the formula (I) that is formed and of the at least one hydroxy compound of the formula (I) used in a stoichiometric excess. The process of the invention is thus preferably executed in solution. The at least one hydroxy compound of the formula (I) that throughout the decarboxylation reaction is present in a stoichiometric excess relative to the carboxylic acid compound of the formula (II) serves here as the solvent.

The process of the invention can be a batch process, semi-batch process or continuous process.

The process of the invention is preferably used for producing a hydroxy compound of the formula (I) shown above, in which R is a tert-butyl, propyl or methyl group, n is 1 or 2, preferably 1, and m is 0, 1, 2 or 3. The process of the invention is particularly preferably used to produce 4-propylphenol, ortho-, para- or meta-methylphenol (cresols), 2,4-dimethylphenol, 2,5-dimethylphenol, 4-tert-butylphenol or phenol. The process of the invention is very particularly preferably characterized in that the hydroxy compound of the formula (I) is phenol.

It is also preferable that the at least one hydroxy compound of the formula (I) that throughout the decarboxylation reaction is present in a stoichiometric excess relative to the carboxylic acid compound of the formula (II) is—if present—a hydroxy compound of the formula (I) shown above, in which R is a tert-butyl, propyl or methyl group, n is 1 or 2, preferably 1, and m is 0, 1, 2 or 3. This at least one hydroxy compound of the formula (I) that throughout the decarboxylation reaction is present in a stoichiometric excess relative to the carboxylic acid compound of the formula (II) is particularly preferably 4-propylphenol, ortho-, para- or meta-methylphenol (cresols), 2,4-dimethylphenol, 2,5-dimethylphenol, 4-tert-butyl-phenol or phenol. Very particular preference is given to phenol.

It is preferable that the hydroxy compound of the formula (I) produced by the process of the invention corresponds to the hydroxy compound of the formula (I) that throughout the decarboxylation reaction is present in a stoichiometric excess relative to the carboxylic acid compound of the formula (II).

In accordance with the invention, the carboxylic acid compound of the formula (II) or the salt of the carboxylic acid compound of the formula (II) are occasionally also collectively referred to as the carboxylic acid compound of the formula (II). However, unless otherwise stated, this always means the free acid and/or the salt. According to the invention, it is also possible to use mixtures of different carboxylic acid compounds of the formula (II) or of different salts of the carboxylic acid compounds of the formula (II) or else mixtures of at least one carboxylic acid compound of the formula (II) with at least one salt of the carboxylic acid compound of the formula (II).

In the process of the invention it is preferable that the cation of the salt of the carboxylic acid compound of the formula (II) is selected from the group consisting of alkali metal cations, alkaline earth metal cations, ammonium, phosphonium, cations of manganese, iron, cobalt, nickel, copper, zinc, molybdenum, cadmium, and any desired mixtures thereof. The cation of the salt of the carboxylic acid compound of the formula (II) is particularly preferably selected from the group consisting of alkali metal cations, alkaline earth metal cations, and mixtures thereof.

In addition, it is preferable according to the invention that the carboxylic acid compound of the formula (II) or the corresponding salt of the carboxylic acid compound of the formula (II) is selected from the group consisting of 2-hydroxybenzoic acid, 4-hydroxybenzoic acid, and the corresponding salts. Very particularly preference is given to 4-hydroxybenzoic acid or the corresponding salt.

In one aspect of the invention, it is further preferable that the carboxylic acid compound of the formula (II) or the corresponding salt of the carboxylic acid compound of the formula (II) was obtained by fermentation or from sugars, lignocellulose, lignocellulose-containing materials, furans, and/or lignin. The carboxylic acid compound of the formula (II) or the corresponding salt of the carboxylic acid compound of the formula (II) is thus preferably biobased. For the purposes of the present invention, the expression "biobased" is understood as meaning that the relevant chemical compound is at the filing date available and/or obtainable via a renewable and/or sustainable raw material and/or preferably is such a renewable and/or sustainable raw material. A renewable and/or sustainable raw material is preferably understood as meaning a raw material that is regenerated by natural processes at a rate that is comparable to its rate of depletion (see CEN/TS 16295:2012). The expression is used in particular to differentiate it from raw materials produced from fossil raw materials, also referred to in accordance with the invention as petroleum-based. Whether a raw material is biobased or petroleum-based can be determined by the measurement of carbon isotopes in the raw material, since the relative amounts of the carbon isotope C14 are lower in fossil raw materials. This can be done, for example, in accordance with ASTM D6866-18 (2018) or ISO16620-1 to −5 (2015) or DIN SPEC 91236 2011-07.

In accordance with the invention, the term "petroleum-based" is preferably used to describe those compounds that have a C14 isotope content of less than $0.3 \times 10^{-12}$, particularly preferably of $0.2 \times 10^{-12}$, and very particularly preferably of $0.1 \times 10^{12}$.

Those skilled in the art know how to obtain the carboxylic acid compound of the formula (II) or the corresponding salt of the carboxylic acid compound of the formula (II) by fermentation or from sugars, lignocellulose, lignocellulose-containing materials, furans, and/or lignin.

This is described for example in WO 2015174446, WO 2015156271, US20040143867, Appl. Environ Microbiol 84 2018:e02587-17, WO2016114668, Biomass and Bioenergy 93:209-216 October 2016, Biotechnol Bioeng. 2016 July; 113(7):1493-503, ACS Catal., 2016, 6 (9), pp. 6141-6145 or Biotechnol. Bioeng., 113: 1493-1503, Appl Microbiol Biotechnol. 2018 October; 102(20):8685-8705, Microbiology. 1994 April; 140 (Pt 4):897-904, Journal of Biotechnology 132 (2007) 49-56, WO2000018942, U.S. Pat. No. 6,030,819, EP2698435, Bioprocess Biosyst Eng (2017) 40: 1283, U.S. Pat. Nos. 2,996,540, 9,206,449, Nature 2014, 515, 249-252, Biomass and Bioenergy 93 (2016) 209-216, 3 Biotech. 2015 October; 5(5):647-651, Appl Environ Microbiol. 2018 Mar. 15; 84(6): e02587-17, U.S. Pat. No. 3,360,553A.

In this aspect of the invention, it is particularly advantageous that the use of a biobased carboxylic acid compound of the formula (II) or of a corresponding salt of the carboxylic acid compound of the formula (II) affords a biobased hydroxy compound of the formula (I). This can in turn be used to produce further biobased compounds, for example diaryl carbonates, bisphenols or polycarbonates, ultimately providing access to biobased polymers and allowing them to be produced in an efficient and cost-effective way.

The process of the invention is preferably executed at a pressure between 1 mbar and 1000 mbar, preferably between 5 mbar and 600 mbar, particularly preferably between 10 mbar and 200 mbar. It is also preferable that the process of the invention is executed at a temperature between 180° C. and 400° C., preferably between 180° C. and 270° C., and particularly preferably between 185° C. and 250° C. The decarboxylation reaction is particularly preferably carried out at a reaction temperature of 180° C. and 400° C., preferably between 180° C. and 270° C., and particularly preferably between 185° C. and 250° C., and at a pressure of 1 mbar and 1000 mbar, preferably between 5 mbar and 600 mbar, particularly preferably between 10 mbar and 200 mbar.

Even when further possible process configurations are considered possible by those skilled in the art, it is preferable when the process of the invention is characterized in that it is executed in a distillation column. This offers the advantage that the hydroxy compound of the formula (I) can preferably be taken off as a distillate. In this case, according to the embodiment described above, the bottoms of the distillation column may additionally comprise a hydroxy compound of the formula (I) that throughout the decarboxylation reaction is present in a stoichiometric excess relative to the carboxylic acid compound of the formula (II).

A carboxylic acid compound of the formula (II) or the corresponding salt of the carboxylic acid compound of the formula (II) is then added to the bottoms of the distillation column. Those skilled in the art can realize this without a substantial construction of apparatus. For example, this compound can be added to the bottoms of the distillation column by means of an infeed.

The decarboxylation reaction is now initiated during the distillation. It was found in accordance with the invention that the conditions present in such a distillation column (temperature and pressure) are sufficient to initiate a decarboxylation reaction. The presence of a catalyst is not necessary for this.

The invention is preferably further characterized in that the hydroxy compound of the formula (I) already formed is additionally supplied to the distillation column in impure form and that in the distillation column it is separated from the impurities in addition to the execution of the process of the invention in all configurations and preferences. In this case, a hydroxy compound of the formula (I) is present in the bottoms that throughout the decarboxylation reaction is present in a stoichiometric excess relative to the carboxylic acid compound of the formula (II). This hydroxy compound of the formula (I) that functions as a solvent may contain impurities. These are preferably impurities that arise in the synthesis of bisphenols and/or in the polymerization of polycarbonates by interfacial processes and/or melt processes. Such processes generate secondary streams comprising an impure hydroxy compound of the formula (I). These impurities are therefore also present in the bottoms of the distillation column. A catalytic effect of these impurities in the decarboxylation of a carboxylic acid compound of the formula (II) or of the corresponding salt of the carboxylic acid compound of the formula (II) is currently unknown, therefore these impurities are not understood as being a catalyst for the purposes of the present invention. If the distillation is now carried out, on the one hand the hydroxy compound of the formula (I) already formed undergoes distillation and can be taken off as a distillate. On the other hand, the process of the invention concomitantly results in the formation and concomitant distillation of a hydroxy compound of the formula (I). The net result is thus that a mixture of hydroxy compounds of the formula (I) can be taken off as a distillate, said mixture comprising both the compound already formed before addition to the bottoms and the compound formed in the distillation column. The distillation preferably also separates this mixture from the impurities formerly present in the hydroxy compound of the formula (I) already formed. It will be obvious to those skilled in the art that it is here particularly preferable that the formula (I) that throughout the decarboxylation reaction is present in a stoichiometric excess relative to the carboxylic acid compound of the formula (II) corresponds to the hydroxy compound of the formula (I) that is formed by decarboxylation.

The observation that the decarboxylation reaction can also be carried out without a catalyst thus makes it possible to adapt existing systems such as distillation columns. Where an existing process requires the purification of a hydroxy compound of the formula (I), for example by means of a distillation column, a carboxylic acid compound of the formula (II) or the corresponding salt of the carboxylic acid compound of the formula (II) can simply be added to this. This integration is possible in existing systems without great outlay. The energy that is required for the distillation can at the same time be used to initiate the decarboxylation reaction. The process of the invention thus makes it possible to operate the process in a particularly economic and environmentally friendly manner.

Even if the yields of the decarboxylation without the use of a catalyst should be lower than the yields with a catalyst (this does however also depend on the reaction conditions), the process can still bring significant economic benefits through the integration and joint utilization of energy. At the same time, the distillate is diluted by the formation of a new hydroxy compound of the formula (I) and optionally upgraded as a result of this. This can then be supplied to/fed back into further reactions.

It is preferable that the distillate is supplied to a process for producing a bisphenol, a diaryl carbonate or a polycarbonate. Processes for producing diaryl carbonates or bisphenols are known to those skilled in the art. Diaryl carbonates can be produced for example by reacting the hydroxy compound of the formula (I) with phosgene in a known manner. Bisphenols can be obtained by reacting the hydroxy compound of the formula (I) with a ketone in a known manner. Processes for producing polycarbonates using the hydroxy compound of the formula (I) are also known to those skilled in the art. For example, the hydroxy compound of the formula (I) can be used as a chain terminator in an interfacial process for producing polycarbonate in a known manner.

In these processes, the other reactants, such as the ketones, can likewise be biobased or petroleum-based, preferably biobased. This allows products with different proportions of biobased carbon to be selectively obtained.

There are currently different labels according to the point from which a product may be described as "biobased" (see inter alia the certification program for "biobased" products according to ASTM D6866-18 (2018) or ISO16620-1 to −5 (2015) or DIN SPEC 91236 2011-07 from TÜV Rheinland®). The requirement for these different labels is a certain percentage of biobased carbon in the product. The process of the invention makes it possible to easily adjust the proportion of biobased carbon.

A further aspect of the invention provides a process for producing a bisphenol, which comprises the following steps:
(i) reacting at least one hydroxy compound of the formula (I) with at least one ketone to afford a mixture comprising at least one bisphenol and at least one unreacted hydroxy compound of the formula (I),
(ii) separating the unreacted hydroxy compound of the formula (I) from the at least one bisphenol from the mixture in process step (i) to obtain a stream comprising the unreacted hydroxy compound of the formula (I) and a stream comprising the at least one bisphenol,
(iii) distilling the stream comprising the unreacted hydroxy compound of the formula (I) with the addition of at least one carboxylic acid compound of the formula (II) or of a corresponding salt of said carboxylic acid compound of the formula (II) to the distillation bottoms in order to produce a distillate that comprises the at least one hydroxy compound of the formula (I), and
(iv) supplying the distillate from process step (iii) comprising at least one hydroxy compound of the formula (I) to process step (i).

It is particularly preferable that no catalyst is present in process step (iii).

Preferred bisphenols that can be prepared with the process of the invention are those of the formula (2a)

$$HO-Z-OH \qquad (2a),$$

in which

Z is an aromatic radical having 6 to 30 carbon atoms that may contain one or more aromatic rings, may be substituted, and may contain aliphatic or cycloaliphatic radicals or alkylaryls or heteroatoms as bridging elements.

Z in formula (2a) is preferably a radical of the formula (3)

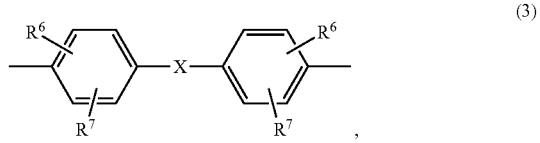

in which $R^6$ and $R^7$ are independently H, $C_1$ to $C_{18}$ alkyl, $C_1$ to $C_{18}$ alkoxy, halogen such as Cl or Br or are each optionally substituted aryl or aralkyl, preferably H or $C_1$ to $C_{12}$ alkyl, particularly preferably H or $C_1$ to $C_8$ alkyl, and very particularly preferably H or methyl, and X is a single bond, $-SO_2-$, $-CO-$, $-O-$, $-S-$, $C_1$ to $C_6$ alkylene, $C_2$ to $C_5$ alkylidene or $C_5$ to $C_6$ cycloalkylidene, which may be substituted by $C_1$ to $C_6$ alkyl, preferably methyl or ethyl, or else $C_6$ to $C_{12}$ arylene, which may optionally be fused with further heteroatom-containing aromatic rings.

X is preferably a single bond, $C_1$ to $C_5$ alkylene, $C_2$ to $C_5$ alkylidene, $C_5$ to $C_6$ cycloalkylidene, $-O-$, $-SO-$, $-CO-$, $-S-$, $-SO_2-$ or is a radical of the formula (3a)

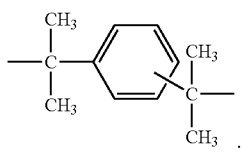

(3a)

Examples of bisphenols are: dihydroxybenzenes, dihydroxydiphenyls, bis(hydroxyphenyl)alkanes, bis(hydroxyphenyl)cycloalkanes, bis(hydroxyphenyl)aryls, bis(hydroxyphenyl) ethers, bis(hydroxyphenyl) ketones, bis(hydroxyphenyl) sulfides, bis(hydroxyphenyl) sulfones, bis(hydroxyphenyl) sulfoxides, 1,1'-bis(hydroxyphenyl) diisopropylbenzenes, and the ring-alkylated and ring-halogenated compounds thereof.

Preferred bisphenols are 4,4'-dihydroxydiphenyl, 2,2-bis(4-hydroxyphenyl)-1-phenylpropane, 1,1-bis(4-hydroxyphenyl)phenylethane, 2,2-bis(4-hydroxyphenyl)propane, 2,4-bis(4-hydroxyphenyl)-2-methylbutane, 1,3-bis[2-(4-hydroxyphenyl)-2-propyl]benzene (bisphenol M), 2,2-bis(3-methyl-4-hydroxyphenyl)propane, bis(3,5-dimethyl-4-hydroxyphenyl)methane, 2,2-bis(3,5-dimethyl-4-hydroxyphenyl)propane, bis(3,5-dimethyl-4-hydroxyphenyl) sulfone, 2,4-bis(3,5-dimethyl-4-hydroxyphenyl)-2-methylbutane, 1,3-bis[2-(3,5-dimethyl-4-hydroxyphenyl)-2-propyl] benzene, and 1,1-bis(4-hydroxyphenyl)-3,3,5-trimethylcyclohexane (bisphenol TMC).

Particularly preferred bisphenols are 4,4'-dihydroxydiphenyl, 1,1-bis(4-hydroxyphenyl)phenylethane, 2,2-bis(4-hydroxyphenyl)propane, 2,2-bis(3,5-dimethyl-4-hydroxyphenyl)propane, 1,1-bis(4-hydroxyphenyl)cyclohexane and 1,1-bis(4-hydroxyphenyl)-3,3,5-trimethylcyclohexane (bisphenol TMC).

In this process, all the preferences and combinations of preferences mentioned above apply also. For the reasons mentioned above, this process is also characterized by high cost-efficiency and environmental friendliness.

EXAMPLES

Chemicals:
4-Hydroxybenzoic acid (4-HBA): Purity≥99%, Sigma-Aldrich Chemie GmbH
Phenol: Purity ≥96%, Sigma-Aldrich Chemie GmbH General Experimental Procedure A 500 mL three-necked flask with a reflux condenser was charged with 150 g of phenol and 150 g of 4-hydroxybenzoic acid and heated to 180° C. under nitrogen and with stirring. At 160° C. a colorless solution was present and the formation of gas bubbles was observed. The solution was heated at 180° C. for 7 hours and samples were taken at regular intervals (see table 1). The samples were dissolved in acetonitrile and analyzed by HPLC (phenol and 4-hydroxybenzoic acid were measured by HPLC using a mixture of 85% by volume of $H_2O+200$ μl $H_3PO_4$ and 15% by volume of acetonitrile as mobile phase at a flow of 1 ml/min on a Zorbax SB-C18 column (with a SpectraSYSTEM pump and a UV detector at 210 nm UV 6000 LP)).

TABLE 1

| Reaction time min | Phenol measured by HPLC % | 4-Hydroxybenzoic acid measured by HPLC % |
|---|---|---|
| 60 | 50.3 | 49.7 |
| 180 | 50.5 | 49.5 |
| 240 | 51.5 | 48.5 |
| 300 | 51.7 | 48.3 |
| 360 | 52.2 | 47.8 |
| 420 | 53.4 | 46.5 |

It can be observed that, under the chosen reaction conditions, 4-hydroxybenzoic acid is converted into phenol even without a catalyst.

The invention claimed is:

1. A process for producing a hydroxy compound of the formula (I)

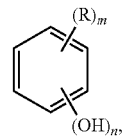

(I)

in which
— R is a linear or branched alkyl group having 1 to 6 carbon atoms,
— n is 1 or 2, and
— m is 0, 1, 2, or 3,
by decarboxylation of a carboxylic acid compound of the formula (II) or of a corresponding salt of said carboxylic acid compound of the formula (II)

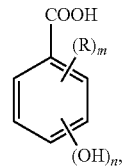

(II)

in which R, n, and m are as defined above,
wherein the decarboxylation is carried out in the absence of a catalyst, and
wherein the process is executed in a distillation column.

2. The process as claimed in claim 1, wherein the decarboxylation is carried out in the presence of at least one solvent.

3. The process as claimed in claim 1, wherein at least one hydroxy compound of the formula (I) is throughout the decarboxylation reaction present in a stoichiometric excess relative to the carboxylic acid compound of the formula (II), the decarboxylation being carried out at a temperature that is above the melting temperature both of the hydroxy compound of the formula (I) that is formed and of the at least one hydroxy compound of the formula (I) used in a stoichiometric excess.

4. The process as claimed in claim 1, wherein the cation of the salt of the carboxylic acid compound of the formula (II) is selected from the group consisting of alkali metal cations, alkaline earth metal cations, ammonium, phosphonium, cations of manganese, iron, cobalt, nickel, copper, zinc, molybdenum, cadmium, and any desired mixtures thereof.

5. The process as claimed in claim 1, wherein the carboxylic acid compound of the formula (II) or the corresponding salt of the carboxylic acid compound of the formula (II) was obtained by fermentation or from sugars, lignocellulose, lignocellulose-containing materials, furans, and/or lignin.

6. The process as claimed in claim 1, wherein the produced hydroxy compound of the formula (I) corresponds to the hydroxy compound of the formula (I) that throughout the decarboxylation reaction is present in a stoichiometric excess relative to the carboxylic acid compound of the formula (II).

7. The process as claimed in claim 1, wherein the hydroxy compound of the formula (I) is phenol.

8. The process as claimed in claim 1, wherein the carboxylic acid compound of the formula (II) or the corresponding salt of the carboxylic acid compound of the formula (II) is selected from the group consisting of 1-hydroxybenzoic acid, 4-hydroxybenzoic acid, and the corresponding salts.

9. The process as claimed in claim 1, wherein the decarboxylation is carried out at a reaction temperature within a range of 180° C. and 400° C. and at a pressure of 1 mbar and 1000 mbar.

10. The process as claimed in claim 1, wherein the hydroxy compound of the formula (I) is taken off as a distillate from the distillation column.

11. The process as claimed in claim 1, wherein the hydroxy compound of the formula (I) already formed is additionally supplied to the distillation column in impure form and that in the distillation column it is separated from impurities.

12. The process as claimed in claim 10, wherein the distillate is supplied to a process for producing a bisphenol, a diaryl carbonate or a polycarbonate.

13. A process for producing a bisphenol, comprising the following steps:
  (i) reacting at least one hydroxy compound of the formula (I) with at least one ketone to afford a mixture comprising at least one bisphenol and at least one unreacted hydroxy compound of the formula (I), the formula (I) is

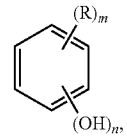

in which
  —R is a linear or branched alkyl group having 1 to 6 carbon atoms,
  —n is 1 or 2, and
  —m is 0, 1, 2, or 3,
  (ii) separating the unreacted hydroxy compound of the formula (I) from the at least one bisphenol from the mixture in process step (i) to obtain a stream comprising the unreacted hydroxy compound of the formula (I) and a stream comprising the at least one bisphenol,
  (iii) distilling the stream comprising the unreacted hydroxy compound of the formula (I) with the addition of at least one carboxylic acid compound of the formula (II) or of a corresponding salt of said carboxylic acid compound of the formula (II) to the distillation bottoms in order to produce a distillate that comprises at least one hydroxy compound of the formula (I), the formula (II) is

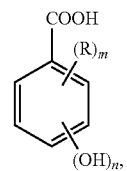

in which R, n, and m are as defined above, and
  (iv) supplying the distillate from process step (iii) comprising at least one hydroxy compound of the formula (I) to process step (i).

14. The process as claimed in claim 13, wherein no catalyst is present in process step (iii).

15. The process as claimed in claim 10, wherein the hydroxy compound of the formula (I) already formed is additionally supplied to the distillation column in impure form and that in the distillation column it is separated from impurities.

16. The process as claimed in claim 15, wherein the distillate is supplied to a process for producing a bisphenol, a diaryl carbonate or a polycarbonate.

* * * * *